United States Patent
Lee et al.

(10) Patent No.: US 6,673,373 B2
(45) Date of Patent: Jan. 6, 2004

(54) ANTIFUNGAL FORMULATION AND THE METHODS FOR MANUFACTURING AND USING THE SAME

(75) Inventors: Fan-Yu Lee, Taichung (TW); Shan-Chiung Chen, Taichung (TW); Ping-Kuen Chen, Taichung (TW); Han-Chiang Kuo, Taichung (TW)

(73) Assignee: Carlsbad Technology Inc., Carlsbad, CA (US)

( * ) Notice: Subject to any disclaimer, the term of this patent is extended or adjusted under 35 U.S.C. 154(b) by 69 days.

(21) Appl. No.: 10/115,994

(22) Filed: Apr. 5, 2002

(65) Prior Publication Data

US 2002/0176894 A1 Nov. 28, 2002

Related U.S. Application Data

(63) Continuation-in-part of application No. 09/774,640, filed on Feb. 1, 2001, now abandoned.

(51) Int. Cl.⁷ .............................. A61N 9/16; A61K 9/50; A61K 31/41; A61K 31/497; A01N 43/64
(52) U.S. Cl. ................. 424/490; 424/493; 424/494; 514/383; 514/254.07
(58) Field of Search .................. 424/490, 493, 424/494; 514/383, 254.07

(56) References Cited

U.S. PATENT DOCUMENTS

| 4,144,346 A | 3/1979 | Heeres et al. |
|---|---|---|
| 4,267,179 A | 5/1981 | Heeres et al. |
| 4,368,200 A | 1/1983 | Heeres et al. |
| 4,503,055 A | 3/1985 | Heeres et al. |
| 4,619,931 A | 10/1986 | Heeres et al. |
| 4,727,064 A | 2/1988 | Pitha |
| 4,791,111 A | 12/1988 | Heeres et al. |
| 4,916,134 A | 4/1990 | Heeres et al. |
| 5,633,015 A | 5/1997 | Gilis et al. |
| 5,707,975 A | 1/1998 | François et al. |
| 5,985,906 A | 11/1999 | Meingassner et al. |
| 6,039,981 A | 3/2000 | Woo et al. |
| 6,100,285 A | 8/2000 | Kantor |

FOREIGN PATENT DOCUMENTS

| EP | 0 514 967 A | 11/1992 |
|---|---|---|
| WO | WO 94 05263 A | 3/1994 |
| WO | WO 00 76520 A1 | 12/2000 |

OTHER PUBLICATIONS

XP-002246760.

*Primary Examiner*—Alton N. Pryor
(74) *Attorney, Agent, or Firm*—Fei-Fei Chao; Venable LLP (57) ABSTRACT

The present invention provides novel pharmaceutical compositions for azole antimicrobial drugs such as itraconazole, saperconazole, ketoconazole, and fluconazole. The pharmaceutical compositions are in the form of pellets which comprise a core and a drug emulsion layer, and optionally, a protective layer. The drug emulsion layer contains the azole antimicrobial drug, an emulsifier, a binder, and an absorbent aid. The preferred emulsifier is vitamin E polyethylene glycol succinate. The preferred binder is hydroxypropyl methylcellulose. The preferred absorbent aid is DL malic acid. The drug is dissolved in organic solvents. The preferred organic solvents are ethanol and methylene chloride. The protective layer contains polyethylene glycol (PEG) 20,000, which is coated on the drug emulsion layer.

34 Claims, 2 Drawing Sheets

ANTIFUNGAL FORMULATION AND THE METHODS FOR MANUFACTURING AND USING THE SAME

This Application is a CIP of Ser. No. 09/774,640 filed Feb. 1, 2001 now abandoned.

FIELD OF THE INVENTION

The present invention relates to pharmaceutical compositions which comprise a core and a drug emulsion layer, and, optionally, a protective layer. The preferred core is a round, spherical core which comprises sucrose, lactose, starch, talc, or microcrystalline cellulose or any combination thereof. The preferred drug is an azole antifungal or antibacterial drug. Examples of the azole antifungal or antibacterial drug include, but are not limited to, itraconazole, saperconazole, ketoconazole, and fluconazole. The drug emulsion layer includes the drug, an emulsifier, a binder, and an absorbent aid. The preferred emulsifier is vitamin E polyethylene glycol succinate. The preferred binder is hydroxypropyl methylcellulose. The preferred absorbent aid is DL malic acid. The azole antifungal or antibacterial drug is preferably dissolved in organic solvents, such as ethanol and methylene chloride. The protective layer contains polyethylene glycol (PEG) 20,000 and is coated on the emulsified layer. The present invention also relates to a method for making the pharmaceutical preparation and methods of using the pharmaceutical preparation to treat patients with fungal or bacterial infections.

BACKGROUND OF THE INVENTION

U.S. Pat. No. 4,267,179 discloses a number of 1H-imidazole and 1H-1,2,4-triazole derivatives having antifungal and antibacterial properties. Specifically, a number of heterocyclic derivatives of (4-phenyl-1-piperazinyl-aryloxymethyl-1,3-dioxolan-2-yl) methyl-1H-imidazoles and 1H-1,2,4-triazoles are described. Among these azole compounds and their derivatives, itraconazole, saperconazole, ketoconazole, and fluconazole are currently commercially available. These commercially available azole compounds are known for their broad spectrum of antimicrobial activity. For example, they are found to be highly active against a wide variety of fungi such as *Microsporum canis, Pityrosporum ovale, Ctenomyces mentagrophytes, Trichophyton rubrum, Phialophora verrucosa, Cryptococcus neoformans, Candida tropicalis, Candida albicans, Mucor species, Aspergillus fumigatus, Sporotricum schenckii* and *Saprolegnia species*. They are also active against bacteria, such as *Erysipelotrix insidiosa, Staphylococcus hemolyticus* and *Streptococcus pyogenes*.

Itraconazole is currently commercially available under the trade name Sporanox® in capsule or tablet form from Janssen Pharmaceutica (Beerse, BE). The chemical structure of itraconazole is disclosed in U.S. Pat. No. 4,267,179 as (±)-cis-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one, having the formula of:

Itraconazole is especially known for its activity against a broad range of fungal inductions such as those caused by *Trichophyton rubrum, Tricophyton mentagrophytes, Epidermophyton floccsum* and *Candida albicans*.

The chemical structure of saperconazole is disclosed in U.S. Pat. No. 4,916,134 as (±)-cis-4-[4-[4-[4-[[2-(2,4-difluorophenyl)-2-(1H-1,2,4-triazol-1-ylmethyl)-3-dioxolan-4-yl]methoxy]phenyl]-1-piperazinyl]phenyl]-2,4-dihydro-2-(1-methylpropyl)-3H-1,2,4-triazol-3-one. Saperconazole has antimicrobial activity, in particular against fungi belonging to the genus Aspergillus.

Ketoconazole was the first of the azole antifungal agents to become commercially available. The chemical structure of ketoconazole is disclosed in U.S. Pat. No. 4,144,346 as cis-1-acetyl-4-[4-[[2-(2,4-dichlorophenyl)-2-(1H-imidazole-1-ylmethyl)-1,3-dioxoolan-4-yl]methoxy]phenyl]piperazine. Ketoconazole is an orally active, broad-spectrum antifungal agent. The compound, an imidazole derivative structurally related to miconazole and clotrimazole, impairs the synthesis of ergosterol, which is the principal sterol of fungal cell membranes.

Fluconazole is a water-soluble triazole with greater than 90% bioavailability after oral administration. The chemical structure of fluconazole is disclosed in U.S. Pat. No. 4,404,216 as 2-(2,4-difluorophenyl)-1,3-bis(1H-1,2,4-triazol-1-yl)propan-2-ol. Fluconazole is used extensively to treat a wide range of Candida infections. In particular, it is widely used in connection with therapy for oropharyngeal candidiasis in patients with advanced HIV infection and AIDS.

The solubility and bioavailability of itraconazole and saperconazole are low due to the fact that these compounds have a low solubility in water and a low pKa value. For example, the solubility of itraconazole is less than 1 μg/ml in water and the pKa value of itraconazole is 3.7.

There have been several reports which show improvement of solubility and bioavailability of itraconzole and/or saperconazole. For example, U.S. Pat. No. 6,100,285 describes a solvent system for dissolving itraconazole. The solvent system contains volatile organic acid solvents such as acetic acid and formic acid, with the solvent itself in an aqueous solution of the acid.

U.S. Pat. No. 5,707,975 discloses a pharmaceutical formulation for itraconazole and saperconazole which is said to have improved solubility and bioavailability. The formulation uses cyclodextrins or the derivatives of cyclodextrins (e.g., hydroxypropyl-β-cyclodextrin) as a solubilizer; an aqueous acidic medium as a bulk liquid carrier (such as hydrochloric acid to achieve optimum pH of 2.0±0.1); and an alcoholic co-solvent (e.g., PEG 400) to dissolve the compounds.

U.S. Pat. No. 5,633,015 discloses a pharmaceutical formulation for itraconazole and saperconazole in the form of beads. The beads comprise a central, rounded or spherical core, a coating film, and a seal-coating polymer layer. The core has a diameter of about 600 to about 700 μm (25–30 mesh). The coating film contains a hydrophilic polymer (such as hydroxypropyl methylcellulose) and a drug (e.g., itraconazole and/or saperconazole). The seal-coating polymer layer is applied to the drug coated cores to prevent sticking of the beads, which would have the undesirable effect of a concomitant decrease of the dissolution rate and of bioavailability. The beads use polyethylene glycol (PEG), in particular, PEG 20,000, as the seal-coating polymer.

U.S. Pat. No. 6,039,981 discloses a pharmaceutical composition which comprises a fused mixture of itraconazole and phosphoric acid, a pharmaceutically acceptable carrier, and a surfactant. The fused mixture of itraconazole and phosphoric acid is prepared by heating the mixture to a temperature ranging from 100 to 170° C. to obtain a homogeneous melt mixture.

The present invention provides novel pharmaceutical compositions for an azole antifungal or antibacterial drug which comprise a core and a drug emulsion layer. The drug emulsion layer comprises the azole antifungal or antibacterial drug, an emulsifier, a binder, and an absorbent aid. The present pharmaceutical compositions are distinctively different from that of U.S. Pat. No. 5,707,975 because no cyclodextrin or its derivative is used as a solubilizer. The present pharmaceutical compositions are also different from that of U.S. Pat. No. 5,633,015 because it contains an absorbent aid in the drug emulsion layer. Furthermore, the present pharmaceutical compositions are distinctively different from that of U.S. Pat. No. 6,039,981 because no fusion of itraconazole with phosphoric acid is used.

The present pharmaceutical compositions display similar and/or superior solubility and bioavailability as compared to the commercially available azole antifungal or antibacterial drugs.

SUMMARY OF THE INVENTION

The present invention provides two orally administered pharmaceutical preparations in the form of pellets, which can be further encapsulated. The first pharmaceutical preparation comprises a core coated with a drug emulsion layer. Optionally, a protective layer which contains polyethylene glycol (PEG) 20,000 is coated onto the emulsion layer. The core is rounded or spherical in shape, which can be obtained from a bulk drug manufacturer or produced in-house. Examples of the core materials include, but are not limited to, sucrose, lactose, starch, talc, or microcrystalline cellulose or a combination thereof. Optionally, polyvinyl pyrrolidone (PVP K-30) can be used as a plasticizer in combination with the core materials. The drug emulsion layer comprises an azole antifungal or antibacterial drug, an emulsifier, a binder, and an absorbent aid. Examples of the azole antifungal or antibacterial drug include, but are not limited to, itraconazole, saperconazole, ketoconazole, and fluconazole. The preferred weight ratio between the core and the drug is 1:0.2–0.6. Examples of the emulsifier include, but are not limited to, polyoxypropylene-polyoxyethylene block copolymers (e.g., Poloxamer 188), polyethylene-sorbitan-fatty acid esters (e.g., Tween 80), sodium lauryl sulfate, and vitamin E polyethylene glycol succinate. The preferred emulsifier is vitamin E polyethylene glycol succinate. Examples of the binder include, but are not limited to, polyvinyl pyrrolidone (PVP), hydroxypropyl cellulose (HPC), hydroxypropyl methylcellulose (HPMC), and methylcellulose (MC). The preferred binder is HPMC. Examples of the absorbent aid include, but are not limited to, DL-malic acid, citric acid, ascorbic acid, and alginic acid. The preferred absorbent aid is DL-malic acid. The drug is preferably dissolved in organic solvents. Examples of the organic solvents include, but are not limited to, methylene chloride, ethanol, and isopropanol. The preferred organic solvents are a combination use of methylene chloride and ethanol.

The method for making the first pharmaceutical preparation comprises the steps of: (a) obtaining a core; (b) mixing an emulsifier with a binder to form an emulsion; (c) dissolving an azole antifungal or antibacterial drug in organic solvent, followed by mixing the dissolved drug with the emulsion of (b); and (d) spraying (c) onto the core of (a). The protective layer is prepared by dissolving PEG 20,000 in methylene chloride and ethanol, preferably at a ratio of about 1:1–1.1, v/v.

The core of the pharmaceutical preparation is commercially available. Alternatively, it can be produced as follows: (a) dissolving polyvinyl pyrrolidone in isopropanol to produce a binder solution; and (b) spraying the binder solution of (a) onto sucrose particles to form the core. It is recommended that starch and talc be added to the sucrose core at the same time as the binder solution of (a) is sprayed onto the sucrose particles.

The first pharmaceutical preparation can be used for treating patients with a fungal or bacterial infection.

The present invention also provides a second pharmaceutical preparation which comprises: (a) a core; and (b) a coating containing an effective amount of an azole antifungal or antibacterial drug, vitamin E polyethylene glycol succinate as an emulsifier, hydroxypropyl methylcellulose (HPMC) as a binder (which can be replaced with polyvinyl pyrrolidone (PVP), hydroxypropyl cellulose (HPC), or methylcellulose (MC)), and DL-malic acid as an absorbent aid. Optionally, a protective layer can be added on top of the drug coating. The core and the drug are composed of similar or the same materials as those described in the first pharmaceutical preparation. The preferred weight percentage of vitamin E polyethylene glycol succinate is about 0.005–5%, most favorably 0.01–0.2% by weight of the total pharmaceutical preparation. The preferred weight percentage of DL-malic acid is about 0.005–6%, most favorably 0.01–0.02% of the total pharmaceutical preparation. The azole antifungal or antibacterial drug is preferably dissolved in methylene chloride and ethanol. The preferred volume ratio of methylene chloride and ethanol is about 1:1–1.1, v/v.

The method for making the second pharmaceutical preparation comprises the steps of: (a) obtaining a core; (b) dissolving the vitamin E polyethylene glycol succinate with ethanol; (c) adding the HPMC to (b); (d) adding the azole antifungal drug to (c); (e) adding methylene chloride to (d) to form a drug emulsion; and (f) spraying the drug emulsion of (e) onto the core of (a). Optionally, a protective layer can be sprayed onto the emulsion layer. The protective layer contains PEG 20,000, which is dissolved in methylene chloride and ethanol. The method for preparing the core is similar to or the same as that described in the first pharmaceutical preparation.

The second pharmaceutical preparation can also be used in treating patients with fungal or bacterial infection.

DETAILED DESCRIPTION OF THE INVENTION

Azole antifungal or antibacterial agents, such as itraconazole and saperconazole, are extremely low in solubility and bioavailability. Therefore, these agents are difficult to administer orally. Although these agents are frequently prescribed for the treatment of fungal or bacterial infections, they are generally available in topical preparations or in oral formulations with limited bioavailability.

Due to limited bioavailability, it is generally recommended that these drugs be taken after meals to improve their bioavailability because these azole antimicrobial agents have a high binding rate with plasma proteins. For example, itraconazole has a binding rate with plasma proteins of 99.8%, which is also evidenced by the fact that the concentration of itraconazole in blood is about 60% of that in plasma.

The low solubility and bioavailability of itraconazole are also demonstrated by the fact that once itraconazole has been taken by the patients, it takes about 3–4 hours for the drug to reach a peak concentration in plasma. The plasma itraconazole has a half life of about 1 to 1.5 days. Also, itraconazole is primarily metabolized in the liver. However, only one of the metabolites of itraconazole, hydroxy-itraconazole, has been demonstrated in vitro to have antifungal activity. About 3–18% of the itraconazole in its original form is excreted in feces. About or less than 0.03% of the itraconazole in its original form is secreted in urine. About 35% of the itraconazole metabolites are secreted in urine within a week after the uptake of the drug.

The present invention provides novel pharmaceutical compositions for an azole antimicrobial drug such as itraconazole, saperconazole, ketoconazole or fluconazole. The pharmaceutical compositions comprise a core and a coated drug emulsion layer which are characterized and manufactured as follows:

(A) The Core:

The cores are made of rounded or spherical edible particles. Materials suitable for use as cores include, but are not limited to, sucrose, lactose, starch, talc, and microcrystalline cellulose. The cores are obtained either by direct purchase from bulk drug manufacturers or in-house preparation. There are generally three kinds of neutral, edible cores which are commercially available. They are (a) 100% pure sucrose cores; (b) combined sucrose and starch cores; and (c) microcrystalline cellulose cores.

The cores made by in-house preparation generally follow the following manufacturing procedures:

(a) mixing polyvinyl pyrrolidone (PVP) with isopropanol and distilled water until the PVP is completely dissolved;

(b) putting sucrose particles in a fluidized bed granulator (e.g., Glatt or Huttlin) equipped with a spray insert;

(c) mixing starch and talc together;

(d) spraying (a) onto the sucrose particles while at the same time mixing (c) with the sprayed sucrose particles to form the wet cores; and (e) drying the wet cores to form the cores of the compositions.

(B) The Drug Emulsion Layer:

The drug emulsion layer comprises an azole antimicrobial drug, an emulsifier, a binder, and an absorbent aid. The azole antimicrobial drug is generally first dissolved in organic solvent(s). Examples of the organic solvents include, but are not limited to, methylene chloride, ethanol, and isopropanol. The preferred organic solvents are a combination use of methylene chloride and ethanol. The preferred volume ratio between methylene chloride and ethanol is 1:1–1.1.

Examples of the emulsifier include, but are not limited to, vitamin E polyethylene glycol succinate, polyoxypropylene polyoxyethylene block copolymer (e.g., Poloxamer 188), polyethylene-sorbitan-fatty acid esters (e.g., Tween 80), sodium lauryl sulfate, phospholipids, and propylene glycol mono-or-di-fatty acid esters (e.g., propylene glycol dicaprylate, propylene glycol dilaurate, propylene glycol isostearate, propylene glycol laurate, propylene glycol ricinoleate, and propylene glycol caprylic-capric acid diester). Vitamin E polyethylene glycol succinate is the preferred emulsifier.

Examples of the binder include, but are not limited to, polyvinyl pyrrolidone (PVP), hydroxypropyl cellulose (HPC), hydroxypropyl methylcellulose (HPMC), and methylcellulose (MC). HPMC is the preferred binder.

Examples of the absorbent aid include, but are not limited to, DL-malic acid, citric acid, ascorbic acid, and alginic acid. DL-malic acid is the preferred absorbent aid.

The manufacturing procedure for making the drug emulsion layer is as follows:

(a) mixing the absorbent aid with ethanol until the absorbent aid is completely dissolved;

(b) adding the emulsifier to (a), stirring until the emulsifier is completely dissolved;

(c) adding the binder to (b), stirring until the binder is completely dissolved to form an emulsion solution; and (d) adding the azole antimicrobial drug to the emulsion solution of (c), stirring to ensure that the azole antimicrobial drug is evenly distributed in the emulsion solution. This is followed by adding methylene chloride to the drug-containing emulsion solution, stirring until the drug is completely dissolved to form the drug emulsion layer.

The present pharmaceutical compositions are produced by spraying the drug emulsion layer onto the cores. Because the drug emulsion layer increases the contact surface areas for the drug, the pharmaceutical compositions of the present invention have the advantage of generating a higher drug dissolution rate.

Optionally, a protective layer can be sprayed onto the drug emulsion layer. The protective layer is prepared by mixing polyethylene glycol (PEG) 20,000 with an appropriate volume of methylene chloride. Then, an appropriate volume of ethanol is added to and mixed with the PEG 20,000 solution until the PEG 20,000 is completely dissolved. The protective layer is sprayed coated onto the drug emulsion layer.

The following examples describe pharmaceutical compositions using itraconazole as an example of the azole antimicrobial drug, and the process of making the compositions. These examples are for illustrative purposes. They should not be viewed as limitations of the scope of the present invention. Reasonable variations, such as those that occur to a reasonable artisan, can be made herein without departing from the scope of the present invention.

EXAMPLE 1

(A) Materials and Method for Preparation of the Cores:

The cores were prepared using the following ingredients:

| Ingredients | Amount |
|---|---|
| Polyvinyl Pyrrolidone (PVP K-30) | 40 g |
| Isopropyl Alcohol | 300 ml |
| Purified Water | 200 ml |
| Sucrose | 400 g |
| Starch | 800 g |
| Talc | 900 g |

The cores were prepared by a three-step process. The first step included dissolving 40 g of PVP K-30 in 300 ml of isopropyl alcohol with stirring and then mixing with 200 ml of purified water, which produced an emulsion solution [phrase not mentioned]. The second step included mixing 800 g of starch and 900 g of talc together. The final step included putting sucrose into a fluidized bed granulator (such as Glatt or Huttlin) and spraying the PVP K-30 emulsion solution produced in the first step onto the sucrose, while at the same time adding the starch-talc mixture to the sucrose, to form the cores. The cores were further dried under warm air.

(B) Materials and Method for Preparation of the Drug Emulsion Layer:

The drug emulsion layer was prepared using the following ingredients:

| INGREDIENTS | AMOUNT |
|---|---|
| Itraconazole | 545.9 g |
| Vitamin E Polyethylene Glycol Succinate | 4.77 g |
| DL-malic acid | 4.77 g |
| Hydroxypropyl Methylcellulose (HPMC) | 818.85 g |
| Methylene Chloride | 7420 ml |
| Ethanol | 7950 ml |

The drug emulsion solution was prepared by mixing 4.77 g of DL-malic acid with 7950 ml of ethanol until the DL-malic acid was completely dissolved. Then, 4.77 g of vitamin E polyethylene glycol succinate was mixed with the dissolved DL-malic acid solution until the vitamin E polyethylene glycol succinate was completely dissolved. Then, 818.85 g of HPMC was added to and thoroughly mixed with the DL-malic acid and vitamin E polyethylene glycol succinate solution, to which 545.9 g of itraconazole was added. Finally, 7420 ml of methylene chloride was added to the itraconazole-containing mixture to form the drug emulsion solution.

(C) Materials and Method for Preparation of the Protective Layer:

The protective layer was prepared using the following ingredients:

| INGREDIENTS | AMOUNT |
|---|---|
| Polyethylene glycol 20,000 | 98.32 g |
| Methylene chloride | 424 ml |
| Ethanol | 445 ml |

The protective layer solution was prepared by thoroughly mixing 98.32 g of polyethylene glycol 20,000 (PEG 20,000) with 424 ml of methylene chloride. Then 445 ml of ethanol was added to the PEG 20,000 solution and mixed until the PEG 20,000 was completely dissolved.

(D) Method for Making the Pharmaceutical Formulation of Example 1:

The pharmaceutical composition of Example 1 was prepared by putting 912.4 g of the cores as described in (A) into the fluidized bed granulator (such as Glatt). The cores were then spray-coated with the aerosolized drug emulsion solution of (B). After drying, spheres with an outer drug layer were obtained. The resultant spheres were placed in the fluidized bed granulator (such as Glatt) and spray-coated with the aerosolized protective-layer solution as described in (C). After further drying, spheres with cores, the drug-layer and the protective layer were obtained.

The pharmaceutical composition of Example 1 contained a weight ratio between the cores and itraconazole of about 1:0.26. The weight percentages of the cores, itraconazole, vitamin E polyethylene glycol succinate, DL-malic acid and HPMC were about 60.9%, 15.5%, 0.14%, 0.14%, and 23.3%, respectively. It was noted that, as indicated in (D), two solvents, i.e., methylene chloride and ethanol, were used to assist in dissolving itraconazole. The volume ratio between methylene chloride and ethanol to be used for dissolving itraconazole was about 1:0.93. Furthermore, the pharmaceutical composition of Example 1 contained a protective layer, which comprised about 9–13% of polyethylene glycol 20,000 dissolved in methylene chloride and ethanol (about 1:1–1.1, v/v).

EXAMPLE 2

The pharmaceutical composition of Example 2 was prepared according to the procedures described in Example 1 using the following ingredients:

| INGREDIENT | AMOUNT |
|---|---|
| 1. The Cores: | 696.84 g |
| 2. The Drug Emulsion Layer: | |
| Itraconazole | 408 g |
| Vitamin E Polyethylene Glycol Succinate | 0.18 g |
| DL-Malic Acid | 0.18 g |
| Hydroxypropyl Methylcellulose (HPMC) | 619.2 g |
| Methylene Chloride | 5600 ml |
| Ethanol | 6000 ml |
| 3. The Protective Layer: | |
| Polyethylene glycol 20,000 | 75.6 g |
| Methylene chloride | 320 ml |
| Ethanol | 336 ml |

The pharmaceutical composition of Example 2 contained a weight ratio between the core and itraconazole of about 1:0.59. The weight percentages of the cores, itraconazole, vitamin E polyethylene glycol succinate, DL-malic acid and HPMC were 40.4%, 23.7%, 0.01%, 0.01%, and 35.9%, respectively. It was noted that two solvents, i.e., methylene chloride and ethanol, were used to assist in dissolving itraconazole. The volume ratio of methylene chloride and ethanol for use in dissolving itraconazole was about 1:1.07. In addition, the protective layer contains 11.5% by weight of PEG 20,000, which was also dissolved by methylene chloride and ethanol. The volume ratio of methylene chloride and ethanol was about 1:1.05.

EXAMPLE 3

The pharmaceutical composition of Example 3 was prepared using the following ingredients:

| INGREDIENT | AMOUNT |
| --- | --- |
| 1. The Cores: | 921.94 g |
| 2. The Drug Emulsion Layer: | |
| Itraconazole | 545.9 g |
| Hydroxypropyl Methylcellulose (HPMC) | 818.85 |
| Methylene Chloride | 7245 ml |
| Ethanol | 7846 ml |
| 3. The Protective Layer: | |
| Polyethylene glycol 20000 | 93.82 g |
| Methylene chloride | 424 ml |
| Ethanol | 445 ml |

The cores and the protective-layer solution were prepared according to the procedure described in Example 1, supra. The drug emulsion solution was prepared by mixing 818.85 g of HPMC with 7846 ml of ethanol thoroughly. Then, 545.9 g of itraconazole was added to the mixture and mixed thoroughly. The resultant mixture was mixed with 7245 ml of methylene chloride until the mixture was completely dissolved to yield the drug emulsion solution.

Spheres with the cores, the drug layers and the protective layers were produced according to the procedure as described in supra Example 1. The pharmaceutical composition of Example 3 was thus obtained.

The pharmaceutical composition of Example 3 differed from Examples 1–2 for it did not contain vitamin E polyethylene glycol succinate and DL-malic acid. The weight ratio between the core and itraconazole in Example 3 was about 1:0.59. The weight percentages of the cores, itraconazole, and HPMC were 40.3%, 23.%, and 35.8%, respectively. It was noted that two solvents, i.e., methylene chloride and ethanol, were used to assist in dissolving itraconazole. The volume ratio of methylene chloride and ethanol for use in dissolving itraconazole was about 1:1.08. In addition, the protective layer contains about 10.8% by weight of PEG 20,000, which was also dissolved by methylene chloride and ethanol. The volume ratio of methylene chloride and ethanol was about 1:1.05.

In Vitro Dissolution Rate and Human Plasma Concentrations of Itraconazole in Examples 1–3

The dissolution rates (% dissolution) of the itraconazole-containing pharmaceutical compositions described in Examples 1–3 were determined according to the method described in the $22^{nd}$ Edition of U.S. Pharmacopoeia. The results of this test are shown in FIG. 1.

The results indicated that the pharmaceutical compositions as shown in Examples 1–3 provided excellent dissolution of itraconazole. The superior dissolution rate (%) was probably due to (1) the proper amounts of emulsifying agent (i.e., vitamin E polyethylene glycol succinate) and absorbent aid (i.e., DL-malic acid) used in the pharmaceutical composition; and (2) the coating of a protective layer onto the drug-emulsified layer.

Figure 1:
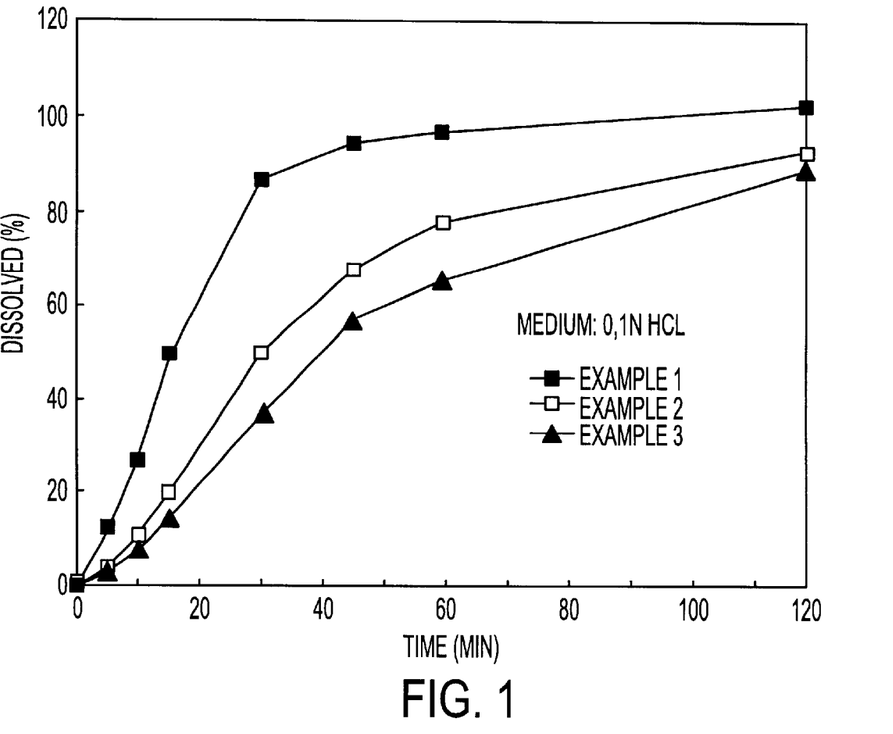
FIG. 1 shows the % dissolution of the formulations in Examples 1 (■, solid square), 2 (□, open square), and 3 (▲, solid triangle) at various time points. The formulations were dissolved in in 0.1 N HCl.

Also, as shown in FIG. 1, the higher weight percentages of both vitamin E polyethylene glycol succinate and DL-malic acid (i.e., 0.14% as in Example 1 vs. 0.01% as in Example 2) demonstrated better % dissolutions. Contrastingly, absence of vitamin E polyethylene glycol succinate and/or DL-malic acid led to a lower dissolution rate, as evident in Example 3.

Figure 2:
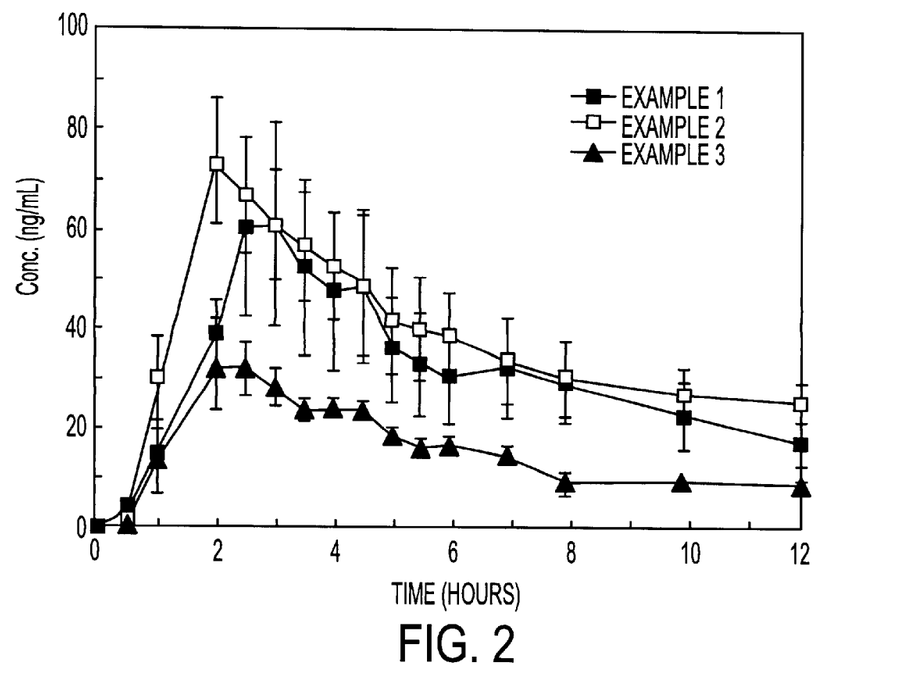
FIG. 2 shows the plasma concentrations of itraconazole (ng/ml) in human after orally administered the formulations of Examples 1 (■, solid square), 2 (□, open square), and 3 (▲, solid triangle). Value=Mean±S.E.

FIG. 2 is a time course of the plasma itraconazole concentrations after a single oral administration of the pharmaceutical compositions of Examples 1–3 in humans. As shown in FIG. 2, Examples 1–2 demonstrated similar plama concentration profiles during the 12-hour study (Example 1 was slightly better than Example 2), which were both significantly better than that of Example 3, which lacked both vitamin E polyhethylene glycol succinate and DL-malic acid.

The overall dissolution rate and plasma drug concentration studies indicated that the pharmaceutical compositions of the present invention provided oral formulations of Example 1–3 that had excellent absorption rate in human.

EXAMPLE 4

The pharmaceutical composition of Example 4 was prepared according to the procedures described in Example 1 using the following ingredients:

| INGREDIENT | AMOUNT |
| --- | --- |
| 1. The Cores: | 1085.00 g |
| 2. The Drug Emulsion Layer: | |
| Itraconazole | 350.00 g |
| Vitamin E Polyethylene Glycol Succinate | 78.75 g |
| DL-Malic Acid | 61.25 g |
| Hydroxypropyl Methylcellulose (HPMC) | 175.00 g |
| Methylene Chloride | 5950 ml |
| Ethanol | 3850 ml |

The pharmaceutical composition of Example 4 contained a weight ratio between the cores and itraconazole of 1:0.32. The weight percentages of the cores, itraconazole, vitamin E polyethylene glycol succinate, DL-malic acid, and HPMC were 60%, 20%, 4.5%, 3.5%, and 10%, respectively. Two solvents, i.e., methylene chloride and ethanol, were used to assist in dissolving itraconazole. The volume ratio between methylene chloride and ethanol was 1.5:1.

EXAMPLE 5

The pharmaceutical composition of Example 5 was prepared according to the procedures described in Example 1 using the following ingredients:

| INGREDIENT | AMOUNT |
| --- | --- |
| 1. The Cores: | 1050.00 g |
| 2. The Drug Emulsion Layer: | |
| Itraconazole | 350.00 g |
| Vitamin E Polyethylene Glycol Succinate | 96.25 g |
| Hydroxypropyl Methylcellulose (HPMC) | 175.00 g |
| Methylene Chloride | 5950 ml |
| Ethanol | 3850 ml |

The pharmaceutical composition of Example 5 contained a weight ratio between the cores and itraconazole of 1:0.33. The weight percentages of the cores, itraconazole, vitamin E polyethylene glycol succinate, DL-malic acid, and HPMC were 60%, 20%, 5.5%, 4.5%, and 10%, respectively. Two solvents, i.e., methylene chloride and ethanol, were used to assist in dissolving itraconazole.

EXAMPLE 6

The pharmaceutical composition of Example 6 was prepared according to the procedures described in Example 1 using the following ingredients:

| INGREDIENT | AMOUNT |
|---|---|
| 1. The Cores: | 1085.00 g |
| 2. The Drug Emulsion Layer: | |
| Itraconazole | 350.00 g |
| Vitamin E Polyethylene Glycol Succinate | 61.25 g |
| DL-Malic Acid | 78.75 g |
| Hydroxypropyl Methylcellulose (HPMC) | 175.00 g |
| Methylene Chloride | 5950 ml |
| Ethanol | 3850 ml |

The pharmaceutical composition of Example 6 contained a weight ratio between the cores and itraconazole of 1:0.32. The weight percentages of the cores, itraconazole, vitamin E polyethylene glycol succinate, DL-malic acid, and HPMC were 62%, 20%, 3.5%, 4.5%, and 10%, respectively. Two solvents, i.e., methylene chloride and ethanol, were used to assist in dissolving itraconazole.

EXAMPLE 7

The pharmaceutical composition of Example 7 was prepared according to the procedures described in Example 1 using the following ingredients:

| INGREDIENT | AMOUNT |
|---|---|
| 1. The Cores: | 1050.00 g |
| 2. The Drug Emulsion Layer: | |
| Itraconazole | 350.00 g |
| Vitamin E Polyethylene Glycol Succinate | 78.75 g |
| DL-Malic Acid | 78.75 g |
| Hydroxypropyl Methylcellulose (HPMC) | 192.50 g |
| Methylene Chloride | 5950 ml |
| Ethanol | 3850 ml |

The pharmaceutical composition of Example 7 contained a weight ratio between the cores and itraconazole of 1:0.33. The weight percentages of the cores, itraconazole, vitamin E polyethylene glycol succinate, DL-malic acid, and HPMC were 60%, 20%, 4.5%, 4.5%, and 11%, respectively. Two solvents, i.e., methylene chloride and ethanol, were used to assist in dissolving itraconazole.

EXAMPLE 8

The pharmaceutical composition of Example 8 was prepared according to the procedures described in Example 1 using the following ingredients:

| INGREDIENT | AMOUNT |
|---|---|
| 1. The Cores: | 1085.00 g |
| 2. The Drug Emulsion Layer: | |
| Itraconazole | 350.00 g |
| Vitamin E Polyethylene Glycol Succinate | 78.25 g |
| DL-Malic Acid | 78.75 g |
| Hydroxypropyl Methylcellulose (HPMC) | 157.50 g |
| Methylene Chloride | 5950 ml |
| Ethanol | 3850 ml |

The pharmaceutical composition of Example 8 contained a weight ratio between the cores and itraconazole of 1:0.32. The weight percentages of the cores, itraconazole, vitamin E polyethylene glycol succinate, DL-malic acid, and HPMC were 62%, 20%, 4.5%, 4.5%, and 9%, respectively. Two solvents, i.e., methylene chloride and ethanol, were used to assist in dissolving itraconazole.

EXAMPLE 9

The pharmaceutical composition of Example 9 was prepared according to the procedures described in Example 1 except that no vitamin E polyethylene glycol succinate was added to the drug emulsion layer using the following ingredients:

| INGREDIENT | AMOUNT |
|---|---|
| 1. The Cores: | 1048.00 g |
| 2. The Drug Emulsion Layer: | |
| Itraconazole | 320.00 g |
| DL-Malic Acid | 72.00 g |
| Hydroxypropyl Methylcellulose (HPMC) | 160.00 g |
| Methylene Chloride | 5440 ml |
| Ethanol | 3520 ml |

The pharmaceutical composition of Example 9 contained a weight ratio between the cores and itraconazole of 1:0.31. The weight percentages of the cores, itraconazole, DL-malic acid, and HPMC were 65.5%, 20%, 4.5%, and 10%, respectively. Two solvents, i.e., methylene chloride and ethanol, were used to assist in dissolving itraconazole.

EXAMPLE 10

The pharmaceutical composition of Example 10 was prepared according to the procedures described in Example 1 except that polyethylene glycol (PEG 20,000) was used to replace DL-malic acid as the absorbent aid using the following ingredients:

| INGREDIENT | AMOUNT |
|---|---|
| 1. The Cores: | 416.25 g |
| 2. The Drug Emulsion Layer: | |
| Itraconazole | 150.00 g |
| Vitamin E Polyethylene Glycol Succinate | 33.75 g |
| Polyethylene Glycol (PEG 20,000) | 75.00 g |
| Hydroxypropyl Methylcellulose (HPMC) | 75.00 g |

| INGREDIENT | AMOUNT |
| --- | --- |
| Methylene Chloride | 2250 ml |
| Ethanol | 1500 ml |

The pharmaceutical composition of Example 10 contained a weight ratio between the cores and itraconazole of 1:0.36. The weight percentages of the cores, itraconazole, vitamin E polyethylene glycol succinate, polyethylene glycol (PEG 20,000), and HPMC were 55.5%, 20%, 4.5%, 10%, and 10%, respectively. Two solvents, i.e., methylene chloride and ethanol, were used to assist in dissolving itraconazole.

EXAMPLE 11

The pharmaceutical composition of Example 11 was prepared according to the procedures described in Example 1 using the following ingredients:

| INGREDIENT | AMOUNT |
| --- | --- |
| 1. The Cores: | 1028.00 g |
| 2. The Drug Emulsion Layer: | |
| Itraconazole | 412.00 g |
| Vitamin E Polyethylene Glycol Succinate | 90.00 g |
| DL-Malic Acid | 90.00 g |
| Hydroxypropyl Methylcellulose (HPMC) | 180.00 g |
| Methylene Chloride | 4000 ml |
| Ethanol | 4000 ml |

The pharmaceutical composition of Example 11 contained a weight ratio between the cores and itraconazole of 1:0.40. The weight percentages of the cores, itraconazole, vitamin E polyethylene glycol succinate, DL-malic acid, and HPMC were 57%, 23%, 5%, 5%, and 10%, respectively. Two solvents, i.e., methylene chloride and ethanol, were used to assist in dissolving itraconazole.

Dissolution Test on the Pharmaceutical Compositions of Examples 4–11

The dissolution rates (% dissolution) of the itraconazole-containing pharmaceutical compositions described in Examples 4–11 were determined and compared to that of Sporanox® capsules, the brand name itraconazole capsules, according to the method described in the 22$^{nd}$ Edition of U.S. Pharmacopoeia. The results of this test are shown in Table 1.

TABLE 1

| | % DISSOLUTION OF EXAMPLES 1–11 | | |
| --- | --- | --- | --- |
| | % Dissolution at 0.1 N HCl | | |
| EXAMPLE # | 45 minutes | 60 minutes | 120 minutes |
| 4 | 35.35 | 41.65 | 62.73 |
| 5 | 29.42 | 34.17 | 41.45 |
| 6 | 35.55 | 44.87 | 67.89 |
| 7 | 46.58 | 59.64 | 92.65 |
| 8 | 44.08 | 56.08 | 86.75 |
| 9 | 8.12 | 12.63 | 41.46 |
| 10 | 15.96 | 17.19 | 19.08 |
| 11 | 34.23 | 42.67 | 63.90 |
| Sporanox ® | 47.33 | 61.10 | 86.44 |

As shown in Table 1, only the % dissolution rate of Examples 7–8 were comparable to that of Sporanox®, as determined in 1N HCl at 45, 60, and 120 minutes. The rest of the Examples showed much lower % dissolution rates than that of the Sporanox® capsules at the same time intervals. Since the pharmaceutical composition of Examples 7–8 both contained vitamin E polyethylene glycol succinate and DL-malic acid, it could reasonably be concluded that both vitamin E polyethylene glycol succinate and DL-malic acid were necessary for the pharmaceutical compositions containing itraconazole to achieve higher dissolution rates.

This was further evident by the studies of Examples 9–10, which showed much lower dissolution rates than that of the Sporanox® capsule. Example 9 did not contain vitamin E polyethylene glycol succinate. Example 10 did not contain DL-malic acid. Therefore, the dissolution rates in Examples 9–10 demonstrated that absence of either vitamin E polyethylene glycol and DL-malic acid resulted in low dissolutions.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. An orally administered pharmaceutical preparation comprising:
 a core; and
 a coating which comprises an effective amount of an azole antifungal or antibacterial drug; an emulsifier; a binder; and an absorbent aid;
 wherein said absorbent aid is one selected from the group consisting of DL-malic acid, citric acid, ascorbic acid, and alginic acid; and
 wherein said core and said antifungal drug has a ratio of about 1:0.2–0.6 by weight.

2. The orally administered pharmaceutical preparation according to claim 1, wherein said azole antifungal or antibacterial drug is dissolved in organic solvents.

3. The orally administered pharmaceutical preparation according to claim 1, wherein said azole antifungal or antibacterial drug is itraconazole, saperconazole, ketoconazole or fluconazole.

4. The orally administered pharmaceutical preparation according to claim 1, wherein said core comprises a core material which is at least one selected from the group consisting of sucrose, lactose, starch, talc and microcrystalline cellulose.

5. The orally administered pharmaceutical preparation according to claim 4, further comprising polyvinyl pyrrolidone (PVP K-30) as a plasticizer.

6. The orally administered pharmaceutical preparation according to claim 1, wherein said emulsifier is one selected from the group consisting of polyoxypropylene-polyoxyethylene block copolymers, polyoxyethylene-sorbitan-fatty acid esters, sodium lauryl sulfate and vitamin E polyethylene glycol succinate.

7. The orally administered pharmaceutical preparation according to claim 1, wherein said binder is one selected from the group consisting of polyvinyl pyrrolidone (PVP), hydroxypropyl cellulose (HPC), hydroxypropyl methylcellulose (HPMC) and methylcellulose (MC).

8. The orally administered pharmaceutical preparation according to claim 2, wherein said organic solvents are at least one selected from the group consisting of methylene chloride, ethanol and isopropanol.

9. The orally administered pharmaceutical preparation according to claim 2, wherein said organic solvents are methylene chloride and ethanol.

10. The orally administered pharmaceutical preparation according to claim 9, wherein said methylene chloride and ethanol is at a volume ratio of about 1:1–1.1.

11. The orally administered pharmaceutical preparation according to claim 1, further comprising a protective layer.

12. The orally administered pharmaceutical preparation according to claim 11, wherein said protective layer comprises polyethylene glycol (PEG) 20,000.

13. A method for making the orally administered pharmaceutical preparation according to claim 2, comprising:
  obtaining said core;
  mixing said emulsifier with said binder to form an emulsion;
  mixing said azole antifungal or antibacterial drug and said organic solvent with said emulsion to form a drug emulsion; and
  spraying said drug emulsion onto said core.

14. The method according to claim 13, further comprising:
  coating a protective layer onto said drug emulsion.

15. The method according to claim 13, wherein said core is obtained by
  dissolving polyvinyl pyrrolidone in isopropanol to produce a binder solution; and
  spraying said binder solution onto sucrose to form said core.

16. The method according to claim 15, further comprising:
  adding starch and talc to said core simultaneously when said binder solution is sprayed onto said sucrose.

17. A method of treating patients with fungal infection comprising orally administering the pharmaceutical preparation according to claim 1 to said patients.

18. A method of treating patients with a bacterial infection comprising orally administering the pharmaceutical preparation according to claim 1 to said patients.

19. A pharmaceutical preparation comprising:
  a core; and
  a coating comprising an effective amount of an azole antifungal or antibacterial drug, vitamin E polyethylene glycol succinate, hydroxypropyl methylcellulose (HPMC), and DL-malic acid.

20. The pharmaceutical preparation according to claim 19, further comprises a protective layer.

21. The pharmaceutical preparation according to claim 20, wherein said protective layer comprises polyethylene glycol (PEG) 20,000.

22. The pharmaceutical preparation according to claim 19, wherein said azole antifungal or antibacterial drug is itraconazole, saperconazole, ketoconazole or fluconazole.

23. The pharmaceutical preparation according to claim 19, wherein said hydroxypropyl methylcellulose (HPMC) is replaced with polyvinyl pyrrolidone (PVP), hydroxypropyl cellulose (HPC) or methylcellulose (MC).

24. The pharmaceutical preparation according to claim 19, wherein said core comprises at least one selected from the group consisting of sucrose, lactose, starch, talc, and microcrystalline cellulose.

25. The pharmaceutical preparation according to claim 19, further comprising polyvinyl pyrrolidone (PVP K-30) as a plasticizer.

26. The pharmaceutical preparation according to claim 19, wherein said vitamin E polyethylene glycol succinate is about 0.005–5% by weight of the total pharmaceutical preparation.

27. The pharmaceutical preparation according to claim 26, wherein said vitamin E polyethylene glycol succinate is about 0.01–0.2% by weight of the total pharmaceutical preparation.

28. The pharmaceutical preparation according to claim 19, wherein said DL-malic acid is about 0.005–6% by weight of the total pharmaceutical preparation.

29. The pharmaceutical preparation according to claim 19, wherein said DL-malic acid is about 0.01–0.2% by weight of the pharmaceutical preparation.

30. The pharmaceutical preparation according to claim 19, wherein said azole antifungal or antibacterial agent is dissolved in methylene chloride and ethanol.

31. A method for making the pharmaceutical preparation according to claim 22, comprising:
  (a) obtaining said core;
  (b) dissolving said vitamin E polyethylene glycol succinate with ethanol;
  (c) adding said HPMC to (b);
  (d) adding said azole antifungal drug to (c);
  (e) adding methylene chloride to (d) to form a drug emulsion; and
  (f) spraying said drug emulsion of (e) onto said core of (a).

32. The method according to claim 31, wherein said core is obtained by
  dissolving polyvinyl pyrrolidone in isopropanol to produce a binder solution; and
  spraying said binder solution onto sucrose to form said core.

33. A method of treating patients with a fungal infection comprising orally administering to said patients an effective amount of the pharmaceutical preparation according to claim 19.

34. A method of treating patients with a bacterial infection comprising orally administering to said patients an effective amount of the pharmaceutical preparation according to claim 19.

* * * * *